(12) United States Patent
Baumstummler et al.

(10) Patent No.: US 10,774,362 B2
(45) Date of Patent: Sep. 15, 2020

(54) SAMPLE PREPARATION UNIT AND SAMPLE PREPARATION DEVICE

(71) Applicant: Merck Patent GmbH, Darmstadt (DE)

(72) Inventors: Anne Baumstummler, Gertwiller (FR); Marie Pressel, Dachstein (FR); Sandra Laborde, Oberhaslach (FR); David Lehmann, Andolsheim (FR); Gael Waiche, Strasbourg (FR)

(73) Assignee: Merck Patent GmbH, Darmstadt (DE)

( * ) Notice: Subject to any disclaimer, the term of this patent is extended or adjusted under 35 U.S.C. 154(b) by 12 days.

(21) Appl. No.: 15/107,239

(22) PCT Filed: Dec. 4, 2014

(86) PCT No.: PCT/EP2014/003240
§ 371 (c)(1),
(2) Date: Jun. 22, 2016

(87) PCT Pub. No.: WO2015/096885
PCT Pub. Date: Jul. 2, 2015

(65) Prior Publication Data
US 2017/0002395 A1 Jan. 5, 2017

(30) Foreign Application Priority Data
Dec. 23, 2013 (EP) .................................... 13290327

(51) Int. Cl.
*C12Q 1/22* (2006.01)
*B01L 3/00* (2006.01)
(Continued)

(52) U.S. Cl.
CPC .................. *C12Q 1/22* (2013.01); *A61L 2/28* (2013.01); *B01L 3/502* (2013.01); *G01N 1/28* (2013.01);
(Continued)

(58) Field of Classification Search
CPC ..................................... C12Q 1/22; A61L 2/28
(Continued)

(56) References Cited

U.S. PATENT DOCUMENTS 4,036,698 A 7/1977 Bush et al.
4,215,198 A 7/1980 Gordon
(Continued)

FOREIGN PATENT DOCUMENTS

CN 102389581 A 3/2012
JP S59-153171 A 9/1984
(Continued)

OTHER PUBLICATIONS

International Search Report dated Mar. 5, 2016, issued in corresponding PCT/EP2014/003240, 3 pages.
(Continued)

*Primary Examiner* — Kevin Joyner
*Assistant Examiner* — Holly Kipouros
(74) *Attorney, Agent, or Firm* — Millen, White, Zelano and Branigan, P.C.

(57) ABSTRACT

Sample preparation unit, preferably for sterility testing: a housing body including at least two ports adapted to serve as fluid inlet and/or fluid outlet, a membrane support, and a lid part such that a membrane chamber is defined adjacent said membrane support. One of at least two ports is arranged so as to allow a fluid transfer to/from a first volume of the membrane chamber at a position upstream of a membrane to be placed on the membrane support, and the other ports arranged to allow fluid transfer to/from a second volume of said membrane chamber at a position downstream of a membrane to be placed on said membrane support. A movable part is provided on housing body such that the movable part and housing body are movable relative to each other, selectively interrupting/establishing fluid transfer
(Continued)

between at least one of two ports and the membrane chamber.

14 Claims, 6 Drawing Sheets

(51) Int. Cl.
 *A61L 2/28* (2006.01)
 *G01N 1/28* (2006.01)
 *G01N 1/40* (2006.01)
(52) U.S. Cl.
 CPC . *B01L 2200/026* (2013.01); *B01L 2200/0684* (2013.01); *B01L 2300/02* (2013.01); *B01L 2300/041* (2013.01); *B01L 2300/045* (2013.01); *B01L 2300/049* (2013.01); *B01L 2300/0681* (2013.01); *B01L 2300/0832* (2013.01); *B01L 2300/0858* (2013.01); *B01L 2300/168* (2013.01); *B01L 2400/0644* (2013.01); *G01N 2001/4088* (2013.01)
(58) Field of Classification Search
 USPC ....................................................... 435/287.4
 See application file for complete search history.

(56) References Cited

U.S. PATENT DOCUMENTS

| | | | |
|---|---|---|---|
| 4,640,777 A | 2/1987 | Lemonnier | |
| 5,516,648 A | 5/1996 | Malchesky et al. | |
| 2005/0221417 A1* | 10/2005 | Houghton | C12Q 1/22 435/34 |
| 2010/0012589 A1* | 1/2010 | Ribault | B01L 3/502 210/650 |
| 2012/0037669 A1* | 2/2012 | Goetz | A47G 19/34 222/456 |

FOREIGN PATENT DOCUMENTS

| | | |
|---|---|---|
| JP | H01-312991 A | 12/1989 |
| WO | 96/06184 A1 | 2/1996 |

OTHER PUBLICATIONS

Office Action in corresponding Japan application No. 2016-542249 dated Nov. 5, 2018 (1 page).
Office Action in corresponding CN application 2014-0070356 dated Jul. 13, 2018.

\* cited by examiner

FIG. 8M     FIG. 8N
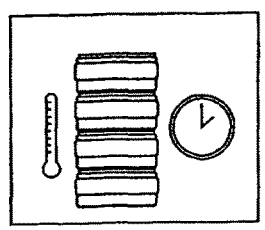
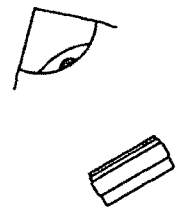
FIG. 9A
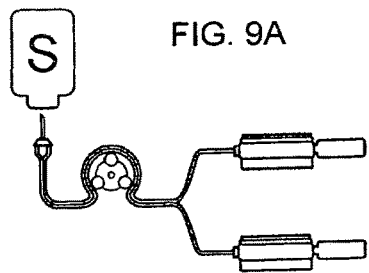
FIG. 9B
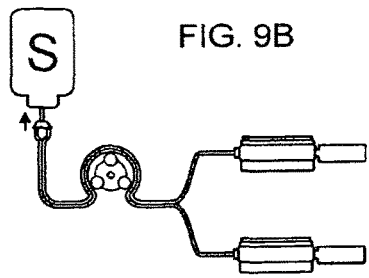
FIG. 9C
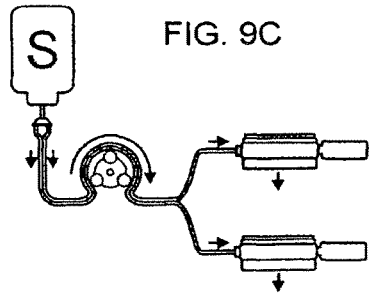
FIG. 9D
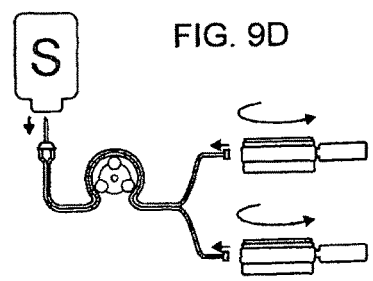
FIG. 9E
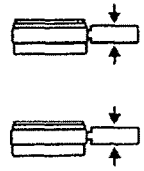
FIG. 9F
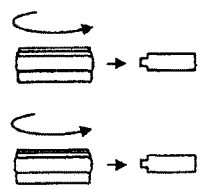

SAMPLE PREPARATION UNIT AND SAMPLE PREPARATION DEVICE

The present invention relates to a sample preparation unit and to a sample preparation device, both preferably for sterility or bioburden testing.

A previous method and an apparatus for sterility testing of solutions, such as antibiotic solutions to determine the presence of microorganisms, is described in U.S. Pat. No. 4,036,698. The apparatus comprises a canister formed as a cylinder of transparent material provided with two ports at one end and each provided with removable sealing caps. One of the ports includes a hydrophobic microporous filter which is supported by a support member. A base member in which a third port is located which is also provided with a removable sealing cap closes an opposite end of the canister. In the method of sterility testing using this apparatus the solution to be tested is flowed through the cylinder having a microporous membrane filter which strains microorganisms from the solution and concentrates them on the microporous filter. Thereafter the cylinder is flushed with a sterile solution, followed by filling the cylinder with an appropriate growth culture medium with the filter being vented, during this step, through a vent having a hydrophobic filter to prevent intake of bacteria. The presence of microorganisms in the original solution to be tested is determined by visual observation of the turbidity of the growth solution after an appropriate incubation period at suitable temperature. Where more than one microorganism is being tested for, aliquots of the test solution are flowed into identical plastic cylinders. The cylinders are intended to be disposable constructed economically enough to be thrown away after each test.

This apparatus and associated method have disadvantages in that the set-up of the system is relatively complex since it requires the external separate connection of numerous components (containers, pumps, valves etc.) via plural segments of tubing. Furthermore, due to the various manual set-up steps the risk of handling mistakes is high and the portion of manual work and thus labor cost is considerable. If all the elements of the system have to be discarded after use, the volume and mass of waste is high which is increasingly problematic under ecological and economical considerations. This system cannot be automated and the apparatus in the form of the canister is bulky and unpractical to handle, especially during incubation and subsequent identification.

Further solutions for some of the above aspects are known in the art but none of these systems has achieved a satisfactory level of efficiency and automation yet.

It is the object of the invention to provide a further improved sample preparation unit and sample preparation device, preferably for sterility or bioburden testing.

The invention accordingly provides, preferably for sterility testing, a sample preparation unit and a sample preparation device. Preferred embodiments of the sample preparation unit and of the sample preparation device are defined in the dependent claims.

The present invention specifically provides a sample preparation unit comprising a housing body including at least two ports adapted to serve as fluid inlet and/or fluid outlet, a membrane support, and a lid part provided such that a membrane chamber is defined adjacent said membrane support by the lid part and the housing body. One of said at least two ports is arranged so as to allow a fluid transfer to/from a first volume of said membrane chamber at a position upstream of a membrane to be placed on said membrane support, and the other of said ports is arranged to allow fluid transfer to/from a second volume of said membrane chamber at a position downstream of the membrane to be placed on said membrane support. A movable part is provided on said housing body such that said movable part and said housing body are movable relative to each other, thereby selectively interrupting/establishing the fluid transfer between at least one of the at least two ports and said membrane chamber.

The provision of the movable part at the housing body and its function to selectively interrupt/establish the fluid transfer between one or both of the at least two ports on the housing body and said membrane chamber facilitates the handling of the sample preparation unit because the ports can be simply closed or opened by the relative movement of the movable part relative to the housing body. Further, it renders superfluous the provision of a number of separate external clamps, valves and sealing caps in a sample preparation system where the sample preparation unit is used because most of these functions are already integrated in the self-contained sample preparation unit. Further, the risk of contamination of the sample in the membrane chamber and thus of a false positive detection result is considerably reduced because the movable part seals the internal volumes of the membrane chamber from the atmosphere and thus avoids the risk of external contamination.

Preferably the movable part and the housing body are rotatable relative to each other. The movable part is in the form of a ring member rotatable about at least part of the periphery of the housing body. The rotatable operation of the movable part, for example in the form of the ring member, reduces the footprint of the unit because it can be concentric with the housing part and guided in a recess of the periphery. Further, the operation is relatively easy and intuitive.

Each of the at least two ports can serve as the inlet or the outlet. Thus, a flow of fluid through the unit can be created in either direction through the at least two ports. Preferably, the sample fluid can be charged from the inlet upstream of the membrane into the membrane chamber and through the membrane to be placed on the membrane support so that the micro-organisms present in the sample are retained on the upper side of the membrane. Preferably a further port can be provided connected to the housing body, for example at the periphery or at the lid part, for establishing a fluid transfer between said further port and the membrane chamber. This further port can be used to add culture media for cell growth or culture media and an indicator for cell growth and rapid detection of the cells in the membrane chamber. A channel allowing the fluid transfer from the further port into the membrane chamber may open at a position above or below the membrane to be placed on the membrane support.

A sealing structure is provided between the movable part and the housing body and is arranged to prevent fluid from escaping from the membrane chamber to the outside through the at least port, preferably through any one of the two or more ports, when the movable part is in a first position, and to allow the selective flow between the at least one port or of selected ones of the ports and the membrane chamber when the movable part is in a second or a further position. Thus, the port or ports can be closed by simply moving the movable part, i.e. by rotating the ring member, so that the unit is completely sealed from the environment and can be safely handled without the danger of contamination.

In a particularly preferred embodiment some or all of the ports are arranged and formed to allow selective separation or disconnection of an external tubing and/or breaking off of an external tubing connected to the respective port(s) at distinct moving positions of the movable part. This variant further facilitates the handling of the unit and the entire process of using the unit in the sample preparation in that the moving of the movable part, i.e. the rotation of the ring member, not only seals the port(s) from the environment but also simultaneously or sequentially disconnects any tubing parts connected to the ports. The defined movability of the ring member, for example, can be used by providing an engaging feature on the moving member, i.e. in the form of a ramp or guide groove, cooperating with a mating engaging feature on the external tubing, i.e. a ridge or other suitable protrusion, to impart a force on the external tubing at the distinct moving position that effects the disconnection.

The membrane support may comprise a drainage channel arrangement, preferably in the form of a spiral or labyrinth or maze, or a porous support on a cavity, preferably a fritted support, wherein at least one of the ports communicates with the volume of the drainage channel arrangement or cavity which is thus a part of the membrane chamber. These structures provide a uniform support to the membrane meant to considerably limit membrane deformation and mechanical stress induced by sample fluid filtration pressure. In the eventual situation of a culture media addition through the port located below the membrane, these structures act as a reservoir making the growth media available to the overall or at least substantial membrane surface so that the entire drainage surface can be saturated with the nutrient medium. The quantity of media adapted to be held below the membrane in case of providing the cavity in combination with the porous support prevents the potential effect of dehydration during incubation of the sample preparation unit and allows continuous bacterial feeding from the drainage channel arrangement or cavity through the pores of the membrane.

Preferably the lid part is at least partly, preferably completely transparent to detection means to allow optical and/or physical inspection of a membrane on the membrane support through the lid part. Thus, the visual bacterial growth detection (e.g. turbidity, colony enumeration, fluorescence, bioluminescence, colorimetric property, spectrophotometric property etc.) can be directly and quickly performed (by the human eye or optical systems and image/pattern detection) in the membrane chamber without opening the sample preparation unit and breaking the sterility. Optionally, the possibility of opening the lid part by removing it from the housing body would allow easy access to the membrane chamber for a further identification process.

Preferably a vent for providing a communication between the outside and the first volume of the membrane chamber and sealed by a gas-permeable membrane may be provided at the periphery of the housing body or at the lid part. The vent may be arranged such that it can be selectively communicated with the membrane chamber, again preferably by arranging the movable part such that it can close the vent at one or several of its moving positions.

The sample preparation unit is preferably formed with an engagement feature at the lid part and/or the bottom of the housing body such that plural sample preparation units can be stacked one on top of another, i.e. in the incubator, and prevented from lateral movement, especially once the external tubing has been removed and the units have been sealed. This feature also allows positional fixation and orientation during automated mechanical handling of the sample preparation units, i.e. during visual inspection.

The present invention also specifically provides a sample preparation device, preferably for sterility testing, comprising at least two sample preparation units according to the invention integrated through a divisible connection part formed between the respective housing bodies or lid parts and separable at a preformed separation section in the connection part. The integration of the two sample processing units with the connection part reduces the number of elements required to set-up a sample preparation system and thus considerably accelerates the sterility testing process. It also increases the sample preparation reliability in that it reduces the number of steps and thus the possible errors on the side of an operator to set-up the system and carry out the various steps described further below in this application and it reduces the number of incidents where the sterility of the system could be potentially impaired.

The integration of plural units in a device provides the possibility of splitting in equal parts the sample fluid between the plural units of one device. After the units of the device have been charged with the sample to be tested, the units are sealed by operating the moving part after being filled with the appropriate culture media and are then separated from each other so that they can be individually stacked on top of each other, thereby reducing the space required during subsequent handling and processing.

Each of the sample preparation units may be provided with a label, e.g. in the form of a barcode, data matrix, QR code or RFID tag, preferably on the respective connection parts that are retained on the respective units after separation, for allowing storing of data related to the respective unit and thus facilitating sample traceability.

The above described sample preparation device may be distributed in a package in a pre-sterilized condition including the external tubing mounted to the respective ports.

BRIEF DESCRIPTION OF DRAWINGS

These and other aspects will become apparent from the description of preferred embodiments described below in connection with the attached drawing. In this drawing:

FIG. 9A-9F show the typical steps of a sterility testing procedure using the sample preparation unit of the present invention in a schematic representation in another embodiment.

Figure 1:
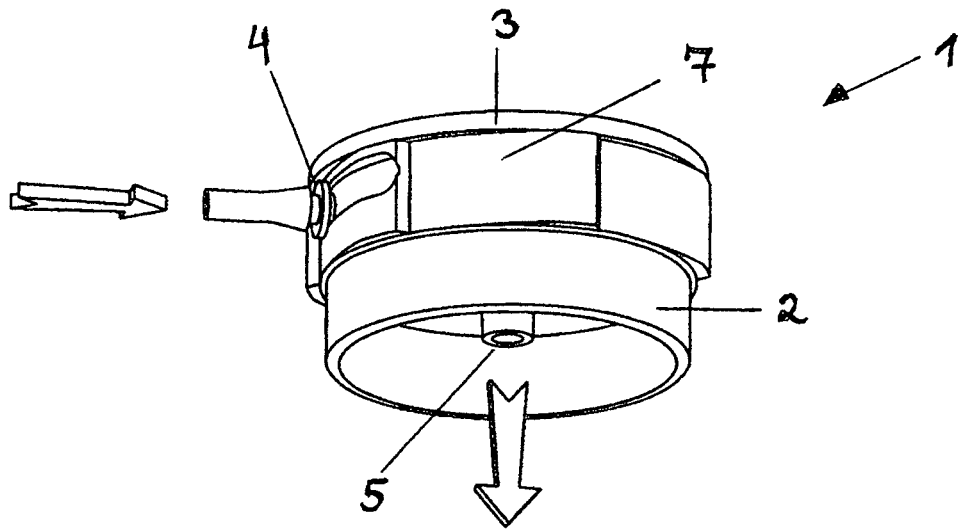
FIG. 1 is a perspective view of a sample preparation unit according to an embodiment of the invention.
Figure 2:
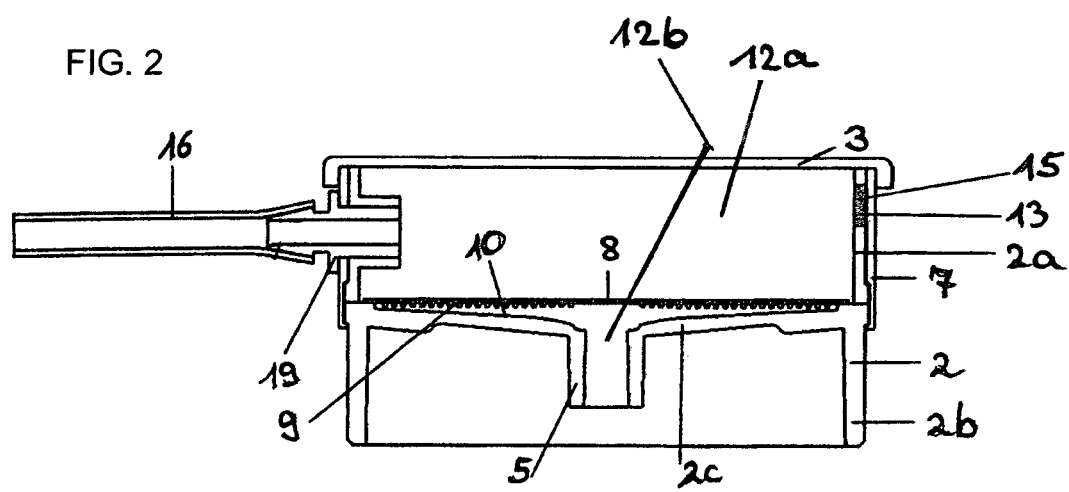
FIG. 2 is a cross-sectional view of the embodiment of FIG. 1.
Figure 3:
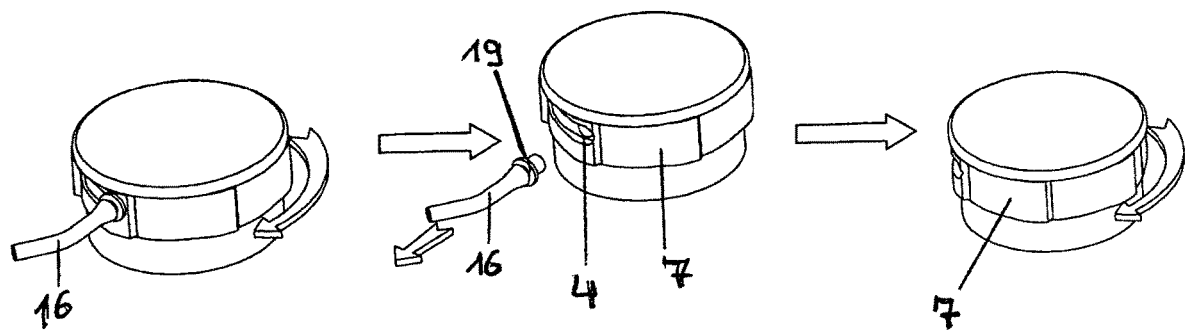
FIG. 3 is a diagram of a sequence of steps comprising tubing separation followed by the sealing of the sample preparation unit of the present invention.

The sample preparation unit 1 according to a first embodiment of the present invention is shown in FIGS. 1 to 3. The sample preparation unit 1 comprises a housing body 2 that defines a membrane support 10 for supporting a membrane 8. The membrane 8 is integrated into the sample preparation unit and is placed on the support 10. The housing body 2 includes at least two ports 4, 5 adapted to serve as fluid inlet and/or fluid outlet of the unit. The housing body 2 also comprises a lid part 3 which, together with the housing body 2 defines a membrane chamber 12 (corresponding to 12a and 12b) and seals the membrane chamber 12 from the environment when the ports are closed as described below. If direct access to the membrane chamber 12 and the upper side of the membrane 8 on the support 10 is desired, the lid part 3 could be detached from the housing body 2, for example, by means of a threaded connection.

Alternative releasable connections like bayonet-type connections or friction-type connections are possible.

The housing body 2 has an overall cylindrical cup shape with a bottom wall 2c, above which the membrane support 10 is formed, and a cylindrical peripheral wall 2a surrounding the membrane chamber 12. A bottom of the housing body 2 is formed with a peripheral collar 2b protruding downward from the outer edge of the bottom wall and beyond a port 5. The peripheral wall 2b mainly serves as a support for the unit and as a protection for the port. It thus does not necessarily have to be a continuous closed wall but can be formed by wall segments or legs or discontinuous protrusions located about the periphery of the base part provided they fulfill the above function. The lid part 3 is provided to close the top of the housing body 2 and thus of the membrane chamber 12.

The housing body 2 of the sample preparation unit 1 is provided with at least one inlet port 4 and at least one outlet port 5. The inlet and outlet ports may be selectively provided and used depending on the process steps to be performed. The inlet port 4 and the outlet port 5 open to a first volume 12a of the membrane chamber 12 upstream or above the membrane 8 and to a second volume 12b of the membrane chamber 12 below or downstream of the membrane 8. The second volume 12b of the membrane chamber 12 is formed by the volume of the spiral or labyrinth channels of the drainage channel arrangement 9 or a cavity below a porous support plate described below. In the sample preparation unit 1 according to the first embodiment one of the ports 4, typically the inlet of the unit, is arranged at the peripheral wall 2a, and the other port 5, typically the outlet of the unit, is arranged at the bottom wall 2c. The bottom wall 2c is inclined downward towards the central port 5 to direct fluid collected downstream of a membrane 8 placed on the membrane support 10 towards the port. A vent 13 for providing a gas communication between the outside and the first volume 12a of the membrane chamber 12 is formed in the peripheral wall 2a of the housing body as shown in FIG. 2. The vent is sealed by a gas-permeable membrane 15. The vent may alternatively be arranged in the lid part 3.

In the embodiment of the sample preparation unit shown in FIGS. 1 and 2 the membrane support 10 includes a drainage structure 9 with a pattern of ribs or convex protrusions defining drainage channels distributed substantially over the entire surface of the support. These channels may be formed like a spiral or in any other labyrinth or maze design as is known in the art in principle. This aspect provides the effect that a liquid medium introduced into the first volume 12a of the membrane chamber 12 through the inlet port 4 upstream of the membrane 8 is evenly distributed or collected below the membrane placed on the support and is guided towards the outlet port 5 in the center of the bottom wall.

In an alternative embodiment (not shown) the support for the membrane may be formed by a porous support plate, i.e. in the form of a fritted support, and a cavity located directly below the porous support plate.

The peripheral wall 2a and the bottom wall 2c with the membrane support 10 and the collar 2b may be integrally formed. However, the bottom wall 2c with the membrane support 10 and the collar 2b can be integrally formed as a base part connected to the peripheral wall 2a formed as a separate part. The connection is made permanent (by gluing or welding or other connections that cannot be separated without destructing the device).

The lid part 3 of the sample preparation unit 1 as shown in the embodiments is at least partly, preferably completely made from a material transparent to detection means to allow optical and/or physical inspection of a membrane 8 placed on the membrane support 10 and/or the liquid enclosed in the first volume 12a of the membrane chamber 12 during the later described reading steps of the sterility testing process, for example. The reading may be performed by the naked eye or through optical detection systems like cameras and digital image analysis or any suitable sensor. It is not required that the entire lid part 3 is made from a transparent material but it is useful that the lid part 3 is at least partly transparent to the detection means.

The form of the lid part 3 and of the peripheral wall 2a may be such that a distance between the transparent portion opposite to the membrane support and the membrane on the support can be minimized as required by the detection means. The lid part or window material and optional surface treatment may be selected to avoid any detection signal perturbation (for example securing low material fluorescence, low luminescence, very high transparency, no mist formation due to temperature change, no diffraction effect).

The sample preparation unit 1 of the invention is provided with a movable part 7 that is of a structure that allows selective opening and sealing of at least one port (typically of the inlet), preferably of all of the ports by a relative movement with respect to the housing body 2. In the first embodiment shown in FIGS. 1 to 3 the movable part is in the form of a ring member 7 rotatable about at least part of the periphery of the housing body 2. The moving part includes a sealing structure that is arranged to prevent fluid from escaping from the membrane chamber 12 to the outside through at least the inlet port 4, preferably through the inlet and outlet ports 4, 5 when the movable part 7 is in a first specific position so that the interior of the unit is sealed from the environment, and to allow the selective flow between the inlet port 4 and the membrane chamber 12 and out through the outlet port 5 when the movable part 7 is in a second specific position. Further moving positions may be provided if additional ports are provided so that they can be selectively opened and closed.

Figure 5:
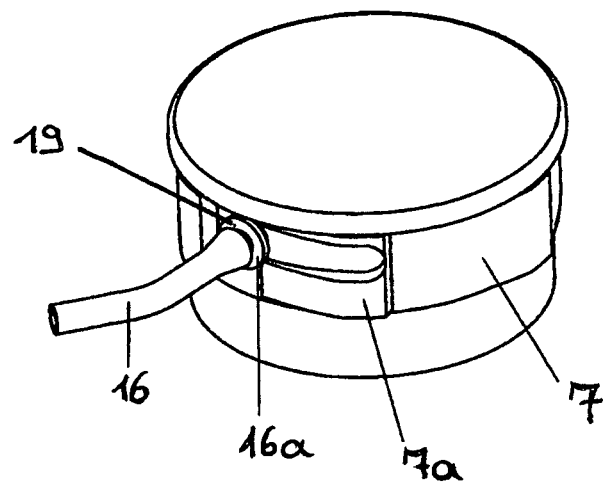
FIG. 5 is an enlarged perspective view of the sample preparation unit of FIG. 1 to explain the feature of the movable part, i.e. for disconnecting an external tubing.

A particularly advantageous structure of the movable part 7 in the sample preparation unit 1 is where some or all of the ports 4, 5 are arranged and formed to allow selective separation or disconnection of external tubing 16 and/or breaking off of external tubing 16 connected to the port 4 at distinct moving positions of the movable part 7 before reaching the position where the ports are fully closed (i.e. the fluid flow is fully interrupted). To achieve that the movable part 7 (i.e. the ring member) includes, as shown in FIGS. 3 and 5 an engaging feature 7a (here in the form of a ramp) designed to cooperate with an engaging feature 16a on the external tubing 16 (here in the form of a peripheral ridge or flange) to impart a force on the external tubing via the flange when the flange rides onto the ramp at the distinct rotating position that pushes the external tubing out of the port and effects the disconnection. Further rotation of the ring member will then close the port opening as shown in FIG. 3 and seal the internal volume of the unit from the environment. The external tubing may be connected to the port via a fitting member 19 that is inserted at one end into the port opening and that is provided at the opposite end with a luer fitting or tube fitting for a removable tube attachment. The fitting member 19 is also provided with the engaging feature 16a so that any type of tubing can be used in combination with the unit of the invention.

Although not shown in the drawing the sample preparation unit may be formed with an engagement feature, for example, in the form of a peripheral protrusion or rim, either continuous or in the form of plural protrusions distributed about the circumference of the lid part and arranged such that plural sample preparation units of the same type can be stacked one on top of another and prevented from lateral movement. Preferably the peripheral collar 2b or discontinuous protrusions at the base parts cooperate with the engagement feature at the top side of the lid part so that the plural sample preparation units can be stacked in regular posture or upside down.

The material and composition of the membrane 8 placed on the membrane support 10 may be chosen according to the intended testing purpose and/or sample to test. A microporous membrane is frequently used for sterility and bioburden testing which is the most preferred field of application of the present invention.

In the sample preparation unit of the invention, after a sample fluid has been introduced into the membrane chamber through the at least two ports and the micro-organisms have been collected on the membrane, a culture medium for promoting the growth of the microorganisms either on the membrane or in the first volume 12a of the membrane chamber 12 can be subsequently injected into the first volume 12a of the membrane chamber 12 or the second volume 12b of the membrane chamber 12 through a respective port of the at least two ports before the unit is sealed at the ports as described above. In an embodiment shown in FIG. 4 a further (third) port 6 for establishing a fluid transfer from the outside of the unit into the membrane chamber 12 can be provided for that purpose and connected to the housing body. The further port 6 can be provided in the peripheral wall 2a, in the lid part 3 or in the base part. Independent from the location of the port on the housing body a channel allowing the fluid transfer from the further port 6 into the membrane chamber 12 may be provided so as to open at a position above or below the membrane 8 placed on the membrane support 10. The further port may be provided such that the movable part 7 opens/closes the port in distinct moving positions. Even the forced disconnection feature described above in connection with the first port 4 can be provided for the third port.

Figure 4:
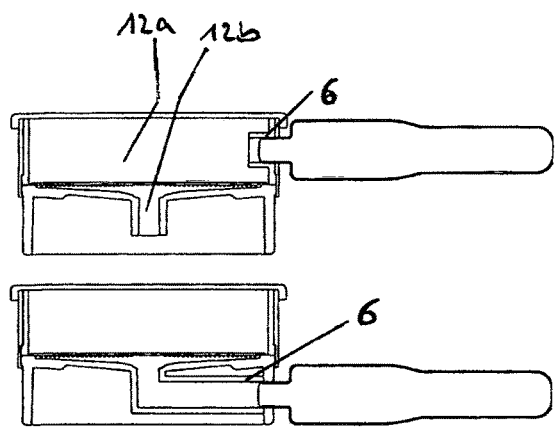
FIG. 4 is a cross-sectional view of two variants of culture medium introduction into the unit.

The representation in FIG. 4 also explains how the second or a third port can be arranged on the outer periphery of the base part and provided with a channel communicating it with the central or another opening at the volume below the membrane support. In this case the ring member can be easily expanded with a sealing structure that allows opening/closing of the second port on the outer periphery as in the case of the first port described above. Also, the forced disconnection feature described above in connection with the first port 4 can be provided for the second or third port.

Figure 6:
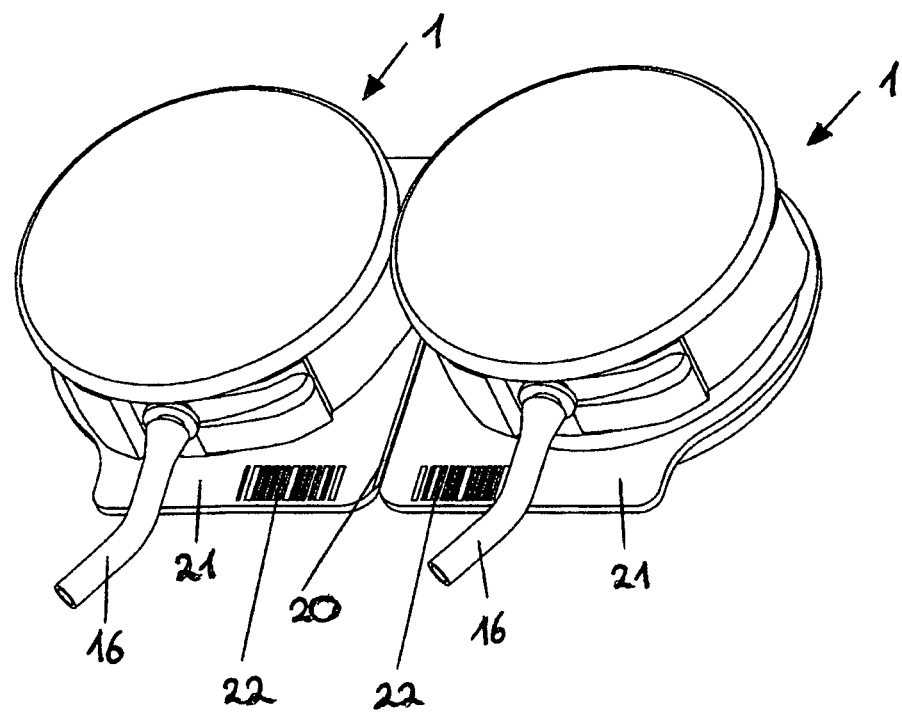
FIG. 6 is a perspective view of a sample preparation device of the invention with two integrated sample preparation units.
Figure 7:
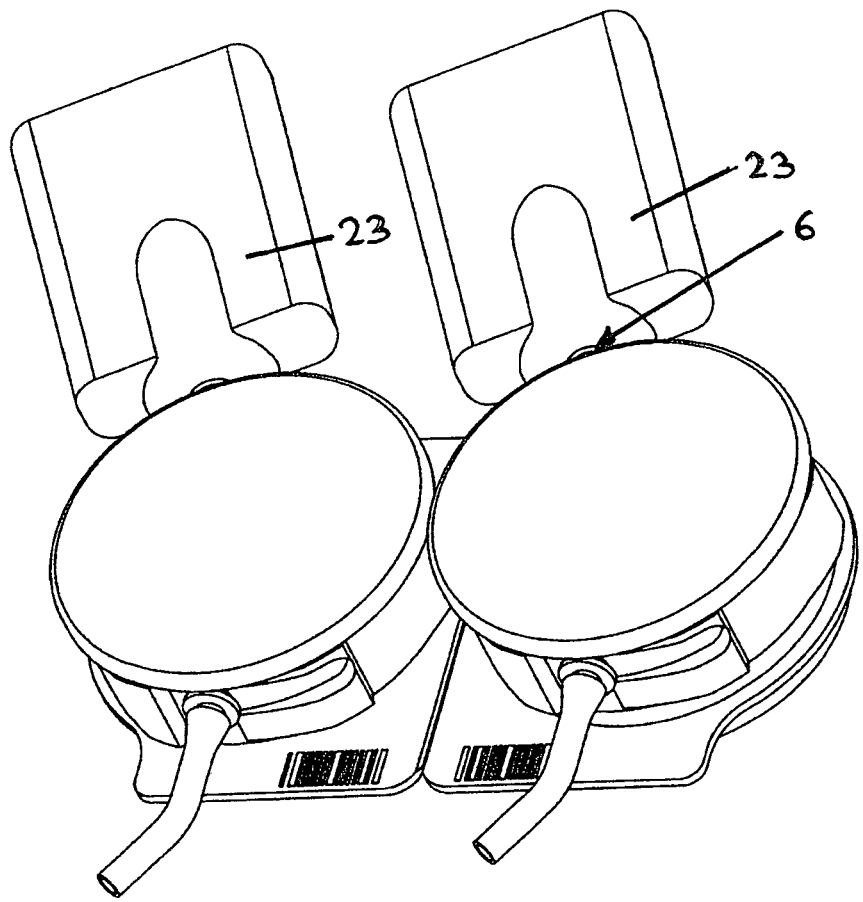
FIG. 7 is a perspective view of a sample preparation device of the invention according to another embodiment with two integrated sample preparation units.

The invention also concerns a sample preparation device as shown in the form of exemplary embodiments in FIGS. 6 and 7 comprising two or more sample preparation units according to the invention. The sample preparation units of the device are all of the same structure and are integrated by a connection part 21 formed between the respective housing bodies 2 or lid parts 3 and are separable through a divisible connection 20, preferably in the form of a preformed separation section in the connection part 21. The connection part 21 may be integrally formed with the housing bodies or may be formed as a separate holder with openings receiving and holding the individual units.

To allow traceability and identification the sample preparation units can be provided with unique identification labels 22, preferably on the respective connection part 21 allowing storing of data related to the respective unit, i.e. in the form of a bar code, data matrix, RFID tag, QR code etc., which can be read either with a manual scan or a scan integrated into any process instrument. This aspect supports easy recording and tracking of processed samples and consumables, media, rinsing fluids and association to a particular test.

As shown in FIG. 7 each sample preparation unit may be provided with a pre-assembled pre-filled vial 23 containing a culture medium. The vial may be pre-connected to a separate port 6 of the unit and the movable part may be configured such that the port is normally closed and opened at a particular moving position following the disconnection of the external tubing from the inlet port and closure thereof as described above.

To provide sterility and efficiency the sample preparation device described above is preferably designed to be disposable. Further, the sample preparation device may be provided with the external tubing for pumping the sample fluid through the unit pre-attached to the respective ports and with the pre-filled vials containing the culture medium pre-attached to the respective ports as well to form a sample preparation system that is pre-sterilized and packaged as a unit. At the point of use the system may be taken out from the package and connected at the inlets and outlets with external fluid containers and pumps or customer samples (vials, bottles, bags, etc.), preferable as described below to carry out a typical sterility testing procedure (FIGS. 8A to 8N).

The following is a description of a typical sample preparation process for sterility testing using the unit of the present invention. The actually used device preferably has two or three or even more sample processing units. For clarity purpose, the illustrations of FIGS. 8A to 8J are not showing the sample preparation device with the sample preparation units linked together as is preferable.

Figure 8A:
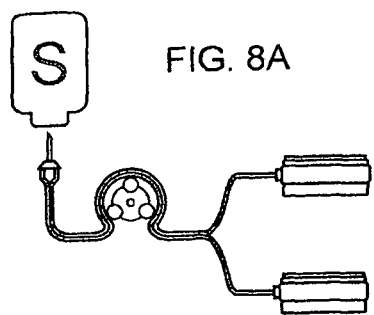
FIG. 8A-8N show the typical steps of a sterility testing procedure using the sample preparation unit of the present invention in a schematic representation in one embodiment.

Initially, the movable part of the sample preparation units is set to a default position where the inlet and outlet ports are in communication with each other through the membrane chamber via the membrane and the sterile vent is closed (FIG. 8A).

Figure 8B:
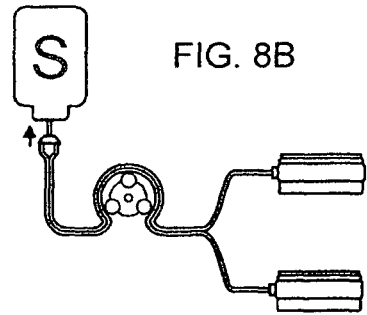
Figure 8C:
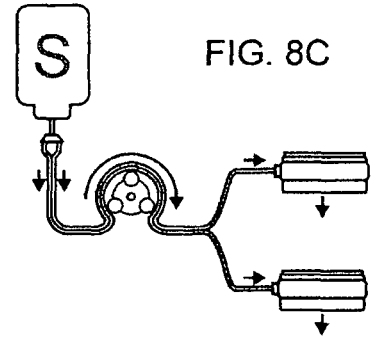

The system is set-up by connecting the sample container "S" to the tubing attached to the inlet ports (FIG. 8B). The sample fluid is transferred from the sample container to the sample preparation units through a peristaltic type pump engaged on the tubing (FIG. 8C). If required, this step can be preceded by a pre-wetting step and/or be followed by a rinsing step both using a rinsing fluid.

Figure 8D:
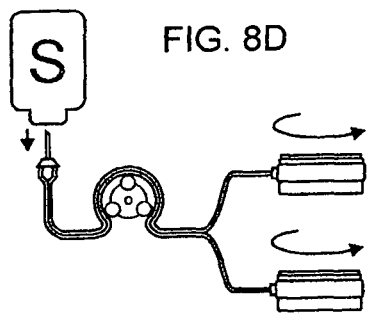
Figure 8E:
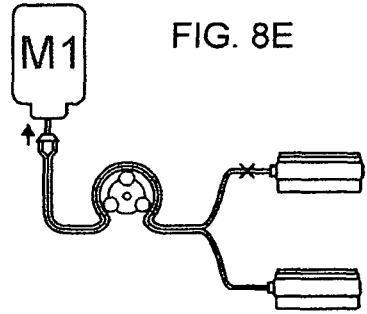
Figure 8F:
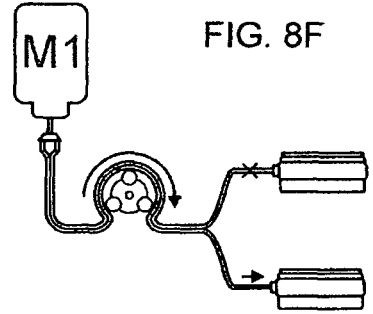
Figure 8G:
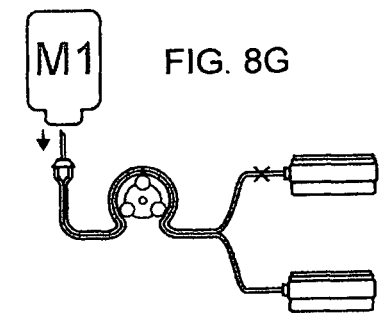
Figure 8H:
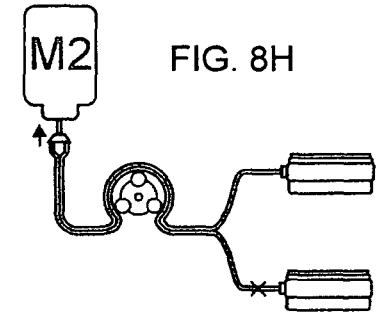
Figure 8I:
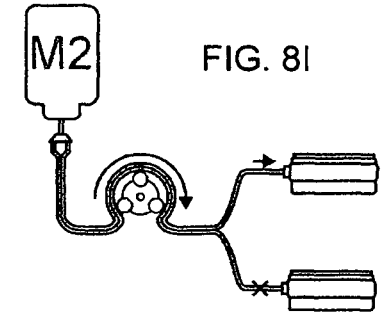

Then, the movable part of the sample preparation unit that should receive a specific growth media is actuated to a position in which the outlet port is closed and the sterile vent is open and the inlet tubing is disconnected from the sample container "S" (FIG. 8D). The tubing attached to the inlet port is then connected to a first growth media container "M1" and the inlet tubing of the other(s) sample preparation unit(s) is closed (e.g. clamp) (FIG. 8E), so the growth media will flow to the chosen sample preparation unit (FIG. 8F). The same procedure is repeated for each of the remaining sample preparation units that are filled with another appropriate growth media, e.g. "M2" (FIGS. 8G-H-I).

Figure 8J:
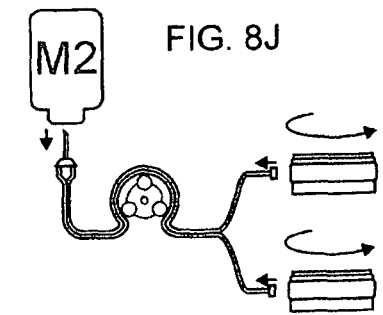

Then, a further actuation of the movable part of the sample preparation unit disconnects the external tubing and seals off the relevant ports (FIG. 8J). From this moment forward, the sample preparation unit's content is isolated from the external environment. At this point, all tubing is discarded.

Figure 8K:
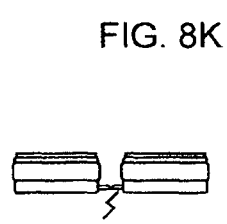

The sample preparation units can be removed and separated by disconnecting the divisible connection holding them together on the sample preparation device (FIG. 8K).

Figure 8L:
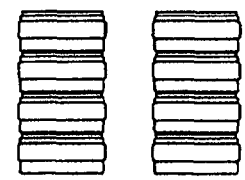

The separated sample preparation units can be grouped in stacks of relevant types of incubation conditions (FIG. 8L) and be placed in an incubator set at a suitable temperature (FIG. 8M).

When the incubation period is over, the sample preparation units are taken out of the incubator and screened for a result, either by bare eye observation or using a detection system (FIG. 8N). The observed results can be safely associated with the original sample by making an advantageous use of the traceability markings on the sample preparation unit (Barcode, Data matrix, QR-Code, RFID tag, etc.).

In a second embodiment (shown in FIGS. 9A to 9F), the growth media vial is pre-attached to the sample preparation unit. In this embodiment, the first steps (sample filtration—FIGS. 9A-B-C) are identical to the previous embodiment. After the filtration step, the sample preparation unit movable part is actuated to disconnect the inlet external tubing and to seal off the corresponding inlet port and the outlet port. Simultaneously, the further port on which a pre-filled culture media vial is pre-assembled is open (FIG. 9D). Then, the user transfers the culture media to the relevant membrane chamber by pressing on the vial (FIG. 9E). Each vial contains a different growth media specific for each sample preparation unit.

Then, a further actuation of the sample preparation unit movable part disconnects the empty culture media vial and closes the further port (FIG. 9F). From this moment forward, the sample preparation unit's content is isolated from the external environment.

Then, the next steps are identical to the corresponding ones of the first embodiment described before (FIGS. 8K-L-M-N).

In case of positive detection, after incubation, the sample preparation units can be opened if so desired by completely removing the lid part from the housing body, i.e. in an aseptic environment like a laminar flow hood or an isolator, to access the first volume of the membrane chamber for further identification purposes. Micro-organisms either in the form of colonies at the surface of the membrane or in suspension in the culture media can be thus easily extracted from the sample preparation unit, i.e. using standard microbiological methods and devices, for further analysis including identification. The sample preparation units can then be discarded as well.

The invention claimed is:

1. A sample preparation unit, comprising:
a housing body including at least two ports adapted to serve as fluid inlet and/or fluid outlet, a microporous membrane placed on a membrane support, and a lid part provided such that a membrane chamber is defined adjacent said membrane support,
wherein one of said at least two ports is arranged so as to allow a fluid transfer to/from a first volume of said membrane chamber at a position upstream of the microporous membrane placed on said membrane support, and the other of said ports is arranged to allow fluid transfer to/from a second volume of said membrane chamber at a position downstream of the membrane placed on said membrane support, and
a movable part provided on said housing body such that said movable part and said housing body are rotatable relative to each other, the movable part being in the form of a ring member rotatable about at least part of the periphery of the housing body thereby selectively interrupting/establishing the fluid transfer between at least one of the at least two ports and said membrane chamber, whereby said sample preparation unit is capable of sterility testing.

2. The sample preparation unit according to claim 1, comprising a further port connected to the housing body establishing a fluid transfer between said further port and said membrane chamber.

3. The sample preparation unit according to claim 2, wherein a channel allowing the fluid transfer from said further port into said membrane chamber opens at a position above or below a membrane to be placed on the membrane support.

4. The sample preparation unit according to claim 1, wherein a sealing structure is provided between the movable part and the housing body and is arranged to prevent fluid from escaping from said membrane chamber to the outside through said at least one port, when the movable part is in a first position, and to allow the selective flow between said at least one port or of selected ones of the ports and the membrane chamber when the movable part is in a second or a further position.

5. The sample preparation unit according to claim 1, wherein the membrane support comprises a drainage channel arrangement, in the form of a spiral or labyrinth or maze, or a porous support on a cavity, wherein at least one of the ports communicates with the volume of the drainage channel arrangement or cavity.

6. The sample preparation unit according to claim 1, wherein the lid part is at least partly transparent to detection means to allow optical and/or physical inspection of a membrane placed on the membrane support.

7. The sample preparation unit according to claim 1, wherein the lid part is either removable from the housing body or is fixedly attached to or integrally formed with the housing body.

8. The sample preparation unit according to claim 1, further comprising a vent providing a communication between the outside and the first volume of said membrane chamber and sealed by a gas-permeable membrane.

9. The sample preparation unit according to claim 8, wherein the movable part is arranged to close said vent at, at least, one of its moving positions.

10. The sample preparation unit according to claim 1, wherein some or all of the ports are arranged and formed to allow selective separation or disconnection of an external tubing and/or breaking off of an external tubing connected to the respective port(s) at distinct moving positions of the movable part.

11. The sample preparation unit according to claim 10, wherein the movable part includes an engaging portion cooperating with an engaging portion on the external tubing to impart a force on the external tubing at the distinct moving position that effects the disconnection.

12. The sample preparation unit according to claim 1, wherein the top of the lid part and/or the bottom of the housing body are formed so as to allow stacking of plural sample preparation units one on top of the other.

13. A sample preparation device comprising at least two sample preparation units according to claim 1 integrated by a connection part formed between the respective housing bodies or lid parts and separable at a divisible connection.

14. The sample preparation device according to claim 13, wherein each of the sample preparation units is provided with a label, on the respective connection part, allowing storing of data related to the respective unit.

* * * * *